United States Patent [19]

Beaver et al.

[11] 4,074,431
[45] Feb. 21, 1978

[54] SURGICAL KNIFE ASSEMBLY, SURGICAL BLADE, AND METHOD OF MANUFACTURE THEREOF

[75] Inventors: John R. Beaver, Lexington; George J. Kozlowski, Bedford, both of Mass.

[73] Assignee: Rudolph Beaver, Inc., Belmont, Mass.

[21] Appl. No.: 678,866

[22] Filed: Apr. 21, 1976

[51] Int. Cl.$^2$ ............................................. B26B 3/00
[52] U.S. Cl. ................................................... 30/353
[58] Field of Search ................. 30/346.57, 349, 351, 30/353; 76/104 R

[56] References Cited

U.S. PATENT DOCUMENTS

| 2,049,898 | 8/1936 | Driest | 30/353 X |
| 3,041,724 | 7/1962 | Bobkowski | 30/353 X |
| 3,346,905 | 10/1967 | Scarpelli | 30/351 X |

Primary Examiner—Jimmy C. Peters
Attorney, Agent, or Firm—R. E. Ross

[57] ABSTRACT

A disposable surgical knife assembly, a blade for use therein, and a method of manufacture thereof. The blade is manufactured in continuous strip form and may be separated from the strip along score lines in predetermined positions so as to provide the blade with a shape that facilitates accurate and automatic assembly into a holder. The holder is provided with a slot in the forward end to receive the rear portion of the blade, which may be retained in the slot by adhesives or by fusion of the holder material into suitable apertures in the blade. A portion of the blade projects laterally therefrom to facilitate adjustment of the blade position in the holder, said portion being readily broken off after completion of assembly.

5 Claims, 4 Drawing Figures

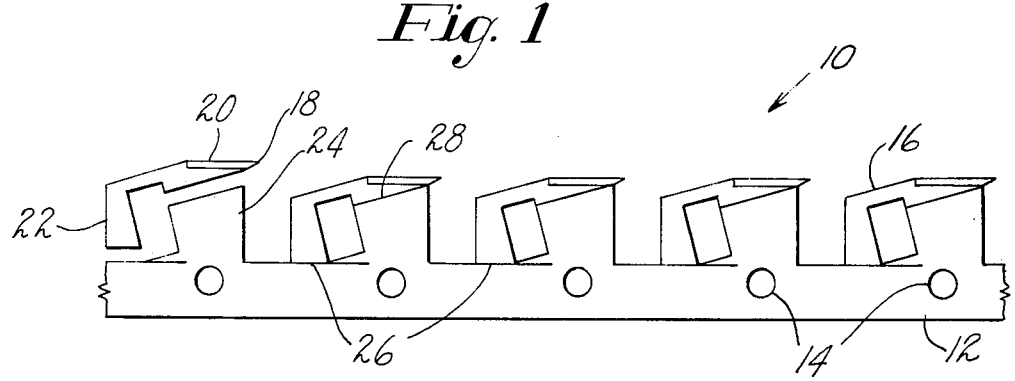
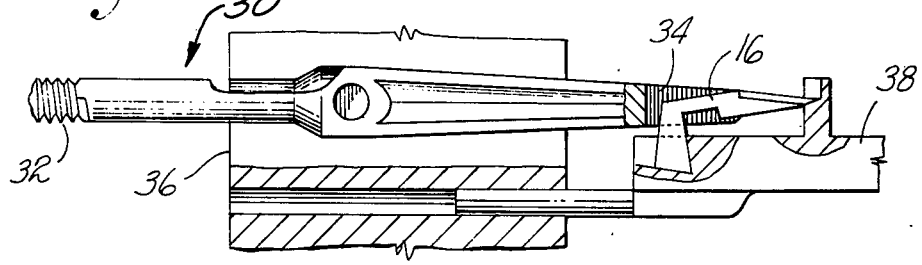
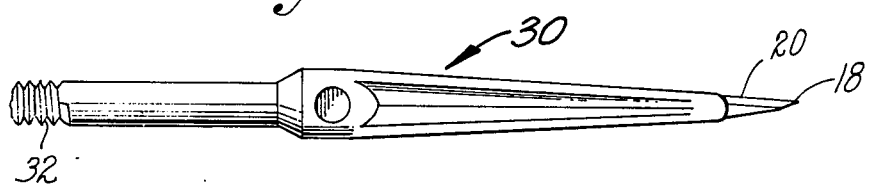
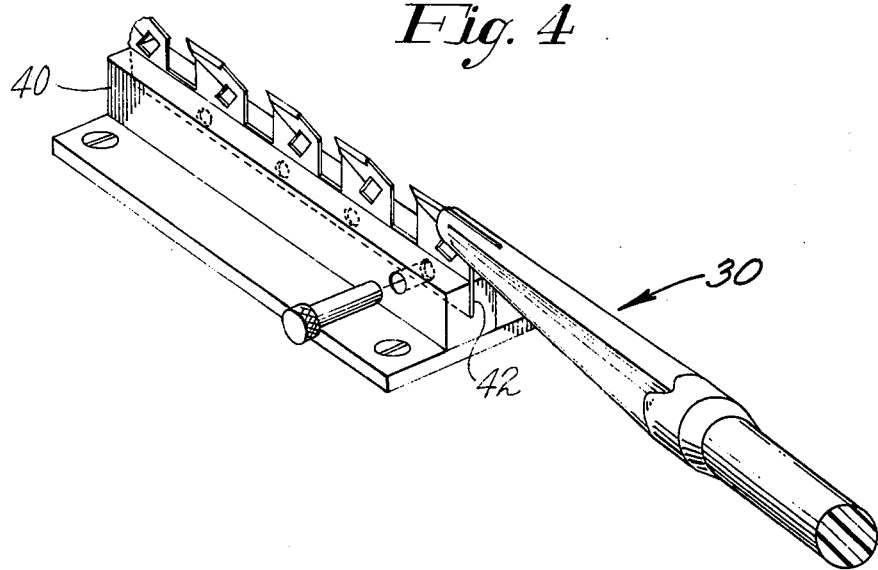

SURGICAL KNIFE ASSEMBLY, SURGICAL BLADE, AND METHOD OF MANUFACTURE THEREOF

BACKGROUND OF THE INVENTION

In certain types of delicate surgical operations, it has been customary to use as a surgical blade a piece of an ordinary carbon steel razor blade of the so-called "safety razor" type. Suitable tools are provided to break off from the blade a shard of desired size, which is then placed into a blade holder. Surgical blades thus made have provided acceptable results in operations such as eye surgery because of the sharpness of the blade and the thinness of the stock from which the blade is formed. The blade is, of course, discarded after a single use.

However, the forming of a blade in this manner and the use thereof has a number of disadvantages. Not every portion of a razor blade edge is suitable for this purpose and the portion to be used must be selected very carefully. The blade shard must be sterilized prior to use, and handled to assemble into the holder after use, which can cause damage to the cutting edge. For example, the sterile blade can be contaminated and dulled by contact with a rubber glove.

Also, the cutting edge on such a shard is not perfectly straight but has a slight curvature resulting from the bending to cause fracture.

In recent years it has become difficult for surgeons to obtain razor blades suitable for this use because of the shift from carbon steel blades to stainless steel blades. Although a piece of a carbon steel blade of proper size can be readily broken off by a suitable tool with a simple bending motion because of the brittleness of the blade, the material of which the stainless steel blades is formed is not as brittle, and hence such blades do not break cleanly, but break with a severe curve imparted to the broken edge. Hence the separation of a piece of desired size from such a blade is sufficiently difficult to be an impractical method of forming a surgical blade with an uncurved cutting tip.

SUMMARY OF THE INVENTION

In accordance with this invention, a surgical blade, a knife assembly utilizing the blade, and methods of manufacture thereof are provided, to produce a surgical knife that is superior to that formed heretofore of a shard of a carbon steel razor blade.

The blade is made in continuous strip form, with the blade being so attached to the strip at scored portions so that it is easily separated therefrom at a predetermined position, providing a blade portion sharpened along one side edge and a tang extending laterally therefrom for use in positioning the blade in a holder. After separation from the strip the blade is assembled into a slot in the end of a suitable holder, and secured therein by heat deformation of the plastic or by an adhesive, or in any other convenient manner. During assembly, the tang may be used to adjust the position of the blade in the holder. In another method of assembly, a blade, while still attached to the strip, is assembled into the holder and thereafter separated from the strip. In this latter method of assembly, the strip is used as the means for adjusting the blade to the proper position in the holder.

BRIEF DESCRIPTION OF THE DRAWINGS

FIG. 1 is plan view of a strip of surgical blades embodying the features of the invention.

FIG. 2 is a view of an individual blade, removed from a strip of blades as shown in FIG. 1, assembled into a blade holder.

FIG. 3 is a plan view of the completed assembly of blade and holder.

FIG. 4 is a perspective view of another method of assembling a blade into the holder.

DESCRIPTION OF THE ILLUSTRATED EMBODIMENT

Referring to FIG. 1 of the drawing there is illustrated a strip 10 comprising a guide portion 12 having suitable registration holes 14, and a series of blades 16 formed therein at spaced intervals.

The blades 16 are formed from the metal of the strip by removing portions thereof by punching, so that each blade comprises a body portion 18 the axis of which is inclined to the axis of the strip with the outer end thereof being parallel to the axis of the strip and sharpened to form a cutting edge 20. The rear end of the blade body portion 18 is connected to the guide portion 12 by a tang 22 that extends laterally in relation to the axis of the body portion, and the forward portion of the blade body portion 18 is connected to a support portion 24 extending from the guide portion.

To facilitate removal of the blade from the guide in a manner to appear hereinafter, the junction between the tang 22 and the guide portion 12 is provided with a scored line 26, and the junction between the body portion 18 and the support portion 24 is provided with a scored line 28.

In the use of such a blade, most of the cutting is done by the extreme forward end portion. An important feature of the illustrated blade configuration is the fact that the extreme forward end portion 19 of the blade 18 extends beyond the support portion 24, so that when the blade is broken away from the support portion along the scored line 28, no bending stress and therefore no deformation is applied to the portion 18.

The strip 10 may be formed from a continuous roll of steel of suitable composition by blanking out the appropriate portions to provide the strip with the configuration of FIG. 1, after which is may be heat treated, if desired, and then passed through sharpening apparatus for forming the cutting edge 20. Since the cutting edge 20 is parallel to the longitudinal axis of the strip, the strip is adapted for passing through standard sharpening apparatus for razor blades or the like.

The provision of the scored connection 28 between the blade and the support portion 24 leaves sufficient strength in the metal to support the blade during the sharpening operation, yet allows separation of the blade from the strip in the manner to be described.

After sharpening the blades are retained on the strip, which may be handled and shipped in roll form, until assembly with a holder 30 in a manner to be described.

In the illustrated embodiment of the invention the holder 30 is formed of synthetic organic plastic, and is provided with threaded means 32 at the rear end for attachment to a handle (not shown) and has a slot 34 at the forward end to receive a blade 16.

In one method of assembly, as illustrated in FIG. 2, the holder 30 may be placed in a nest 36, which positions the forward end of the holder and the slot 34 in predetermined relation to a nest 38 for receiving the tang 22 of a blade 16.

The blade 16 may be separated from the strip by bending the blade out of the plane of the guide portion 12 (or, alternatively, bending the guide portion out of the plane of the blade) until fracture occurs at the score lines 26 and 28. The physical characteristics of the material of the strip is such that fracture will readily occur when the material is stressed by bending, and the presence of the score lines, in providing a line of stress concentration, insures that the break will occur at the desired position.

For this purpose, the strip may be formed of a carbon steel or a heat-treatable stainless steel, heat treated to have a hardness sufficient to enable the material to be broken in the manner described above.

After separation from the strip, the rear end of the blade is placed in the slot of the holder, and positioned so that the tang 22 seats in the nest 36 to accurately position the blade in relation to the holder.

The blade may be retained in the holder in any convenient manner such as by an adhesive, or the plastic at the forward end of the holder may be softened by heat, such as by R.F. heating or sonic welding so that the plastic flows into a suitable recess. Thereafter the tang 22 may be sheared off by any suitable tool. Alternatively, the holder may be injection molded in place on the blade.

In an alternate method of assembly, as illustrated in FIG. 4, the strip 10 may be fed into a guide channel 40, and the holder 30 positioned to receive the blade at the end of the strip. After insertion of the blade into the slot in the holder, the holder may be rotated to separate the blade from the guide strip. In this method of assembly the strip may be indexed forwardly by suitable means to position the end blade in the desired position in the holder where it may be retained by pre-applied adhesive or by any of the above-mentioned methods of fusing the plastic of the holder. The tank 22 may thereafter be removed in a secondary operation.

The remaining protruding portion of the guide portion of the strip may be broken off in any convenient manner, such as by a pair of dies (not shown) operating transversely of the strip.

Although in the illustrated embodiment, the holder is a synthetic organic plastic, it will be understood that a metal holder may be used, with the blade retained mechanically in any convenient manner.

Since certain changes apparent to one skilled in the art may be made in the illustrated embodiment of the invention without departing from the scope thereof it is intended that all matter contained herein be interpreted in an illustrative and not a limiting sense.

I claim:

1. An elongated strip of metal formed into a guide portion and a series of blades extending from an edge of the guide portion at spaced intervals, said blades each having an outer edge extending parallel to the axis of the guide portion and being connected to the guide portion by a weakened portion, said strip being formed of a metal suitably heat treated to provide sufficient brittleness to permit separation of the blade from the strip by bending the blade out of the plane of the strip to cause fracture at the weakened portion.

2. A strip as set out in claim 1 in which the weakened portion is formed by an embossed line.

3. A strip of metal formed into a guide portion and a series of surgical blades extending from a side thereof at spaced intervals, the axis of which blade being inclined to the axis of the strip, one side edge of the blade being attached to the guide portion by a weakened portion, the forward portion of the other side edge being parallel to the axis of the strip and being sharpened to a cutting edge, the extreme forward end of the sharpened portion extending beyond the weakened portion and being unconnected to the guide portion.

4. A strip of metal formed into a guide portion and a series of surgical blades extending from a side thereof at spaced intervals, said blades each comprising a blade portion having one side edge joined to the guide portion of the strip by a weakened portion, part of the other side edge being parallel to the axis of the strip and being sharpened to a cutting edge, and a tang extending from the rear of the blade portion to the guide portion of the strip and being joined thereto by a weakened portion whereby the blade may be readily separated from the strip by bending the blade out of the plane of the guide portion so that fracture occurs at the weakened portion.

5. A strip as set out in claim 4 in which each of said blades is formed of material sufficiently brittle to allow the tang to be readily broken off after assembly of the blade into a holder.

* * * * *